United States Patent [19]

Macdonald

[11] 4,406,766

[45] Sep. 27, 1983

[54] APPARATUS FOR MEASURING THE PH OF A LIQUID

[75] Inventor: Digby D. Macdonald, Columbus, Ohio

[73] Assignee: The Ohio State University, Columbus, Ohio

[21] Appl. No.: 310,515

[22] Filed: Oct. 13, 1981

[51] Int. Cl.³ .......................................... G01N 27/30
[52] U.S. Cl. .................................. 204/433; 204/422; 324/438
[58] Field of Search ............... 204/1 H, 195 S, 195 R, 204/195 F; 324/438

[56] References Cited

U.S. PATENT DOCUMENTS 4,273,637  6/1981  Macdonald et al. ............ 204/195 F Primary Examiner—G. L. Kaplan
Attorney, Agent, or Firm—Millard & Cox

[57] ABSTRACT

An electrode for measuring the pH of a liquid at high temperatures and pressures comprises a first hollow electrode formed of the ceramic which exhibits a pH-dependent potential thereacross and a second electrode provided with a porous ceramic junction. Two flexible-walled members are in fluid communication with the hollow interior of the two electrodes and are surrounded by a chamber whose pressure is kept substantially the same as that to which the electrodes are exposed. However, the chamber is thermally insulated from the hot solution whose pH is being measured. The interiors of the hollow electrodes and the flexible-walled members are filled with the same buffered solution and measuring electrodes are disposed within each of the flexible-walled members. The construction enables the measuring electrodes to be kept at substantially room temperature, thereby reducing chemical attack thereon and eliminates errors in potential measurement due to streaming and thermal diffusion potentials.

12 Claims, 9 Drawing Figures

APPARATUS FOR MEASURING THE pH OF A LIQUID

BACKGROUND OF THE INVENTION

The invention relates to apparatus for measuring the pH of a liquid. More specifically, the invention relates to apparatus capable of measuring the pH of a liquid at high temperatures and pressures.

At temperatures of not more than about 100° C. and at pressure not far removed from atmospheric pressure, the pH of a liquid may be readily determined by means of a conventional glass electrode. However, at temperatures substantially above 100° C., glass electrodes are unusable because the delicate glass membrane upon which the electrode depends is subject to severe chemical corrosion.

It has recently been discovered that certain ceramic membranes may be used in place of glass electrodes for pH measurement in high temperature liquids. A potential difference exists across these ceramic membranes that depends upon the pH of the medium in a manner that is analogous to that for the glass membrane of a glass electrode. Moreover, such ceramic membranes are chemically stable to temperatures in excess of 340° C. and are thus usable for the measurement of pH at such elevated temperatures. A pH electrode using such a ceramic membrane is described in U.S. Pat. No. 4,264,424 issued Apr. 28, 1981 to Niedrach. This patent describes a pH electrode comprising a ceramic membrane defining an internal chamber within which is confined a buffered halide solution. A silver/halide electrode is immersed in the buffered halide solution and electrically connected to a similar silver/silver halide electrode immersed in a halide solution which is in contact, via a porous ceramic plug, with the solution whose pH is to be measured.

Niedrach's electrode suffers from a number of disadvantages. Firstly, the silver/silver halide electrodes are exposed to the high temperature of the solution whose pH is being measured and are thus subject to thermal hydrolysis. Also, if Niedrach's pH electrode is used for measuring a solution under a high and variable pressure, any pressure changes may lead to flow of solution through the porous zirconia junction and consequent mixing of the buffered solution in the reference electrode with the solution being measured. Such physical movement of the solution may produce errors in the potentials recorded by the electrode.

There is thus a need for a pH electrode which can measure pH's at elevated temperatures and pressures without exposing the measuring electrodes to high temperatures and which does not suffer from spurious readings caused by streaming of fluid if pressure changes occur in the liquid whose pH is being measured. The instant invention seeks to provide such a pH electrode.

SUMMARY OF THE INVENTION

The invention provides apparatus for measuring the pH of a liquid at high temperatures and pressures, this apparatus comprising a hollow first electrode formed at least in part of a ceramic capable of exhibiting a pH-dependent potential thereacross and a hollow second electrode at least part of the surface of which is porous. The apparatus of the invention further comprises first and second flexible-walled members each having walls defining a chamber within the flexible-walled member. The chamber within each flexible-walled member communicates with the interior of the associated one of the hollow electrodes but is otherwise fluid tight. First and second measuring electrodes are disposed within the chambers in the flexible-walled members. Pressure equalizing means are provided for substantially equalizing the pressure of a medium surrounding the exterior surfaces of the hollwo electrodes and the pressure of the medium surrounding the flexible-walled members, and thermal insulating means are provided for insulating the first and second flexible-walled members from the temperature of the medium surrounding the hollow electrodes.

In use, the two chambers formed by the chambers in the flexible-walled members and the interiors of the hollow electrodes are filled with the same buffered electrolyte solution. The pressure equalizing means keeps the pressure around the flexible-walled members the same as that around the hollow electrodes and, because of the flexibility of the flexible-walled members, the pressure within the chambers of the flexible-walled members (and thus around the measuring electrodes) is equal to the pressure of the solution which is in contact with the hollow electrodes. Thus, no pressure gradients are present within the chambers formed by the interiors of the hollow electrodes and the chambers within the flexible-walled members, thereby eliminating any flow of fluid through the porous part of the surface of the hollow second electrode. Accordingly, the instant apparatus is not subject to errors due to streaming phenomena. The use of the same buffered electrolyte within the two hollow electrodes eliminates errors due to thermal diffusion potentials, while the thermal insulating means allows the measuring electrodes to remain substantially at room temperature, even though the two hollow electrodes (which are of course exposed to the solution whose pH is being measured) are at temperatures of, for example, 300° C. Accordingly, the apparatus may be used for extended periods with the hollow electrodes in contact with high temperature liquids without any change in the characteristics of the measuring electrodes due to thermal hydrolysis thereof. In the instant apparatus, it is preferred that the buffered electrolyte solution used to fill the hollow electrodes and the chambers within the flexible-walled members be a buffered potassium chloride solution and that the measuring electrodes be silver/silver chloride electrodes. The use of a buffered potassium chloride solution is preferred because the transference numbers of the potassium and chloride ion are both substantially equal to 0.5.

In a preferred form of the instant apparatus, the hollow first and second electrodes are of elongate form and disposed in spaced, side-by-side relationship, one end of each of the hollow electrodes being exposed for contact with a liquid whose pH is being measured and the opposed end of each hollow electrode communicating with its associated hollow flexible-walled member. In such apparatus, the preferred form of pressure equalizing means comprises a conduit extending from adjacent the exposed ends of the hollow electrodes to adjacent the flexible-walled members. Conveniently, this conduit is in the form of a capillary tube disposed between and extending substantially parallel to the two hollow electrodes. This capillary tube permits equalization of pressure between the liquid whose pH is being measured and the medium surrounding the flexible-walled members, but does not permit any substantial transfer of heat from the liquid under test to the flexible-walled members, thereby allowing the flexible-walled members and the measuring electrodes contained therein to be under the same pressure as the liquid under test but at substantially room temperature. To keep the hollow electrodes and the capillary tube of such apparatus in their correct relative positions, conveniently an electrode holder is provided for retaining the hollow electrodes in the proper spaced side-by-side relationship and an enclosure member is provided having walls defining a chamber within which are enclosed the two flexible-walled members. The electrode holder and the enclosure member may conveniently be connected together by one or more elongate, thermally-insulating straps to provide the required degree of insulation between the electrode holder (which will be substantially at the temperature of the liquid being measured) and the enclosure member (which must be kept substantially at room temperature in order that the measuring electrodes may be kept at substantially the same temperature).

As already stated, a variety of ceramic materials are known which develop pH-dependent potentials thereacross when immersed in aqueous solutions, and which may thus be used to form the hollow first electrode of the instant apparatus. Various ceramic materials of this type are described in the aforementioned U.S. Pat. No. 4,264,424 and in the following publications:

Hagenmuller and Van Gool (eds.), "Solid electrolytes", Academic Press, (1978) pp. 291–312;
Edsell and Flengas, Chemical Reviews 70, 339–376 (1970);
U.S. Pat. No. 3,429,962 to Krystyniak;
J. W. Patterson, Journal of the Electrochemical Society 118, 1033–1039 (1971).

The disclosure of these publications is herein incorporated by reference. The preferred ceramic for the hollow first electrode is a zirconia-based ceramic, especially a zirconia/yttrium oxide ceramic. Other possible ceramics for use in the instant apparatus include zirconia stabilzed with calcium oxide, preferably in an amount of about 8 to about 17 weight percent, or a mixture of rare earth oxides. Other ceramics such as doped thorium oxide, doped cerium oxide and doped lanthanium oxide may also be used. As is well known to those skilled in the art, a wide variety of doping agents may be used, for example yttrium oxide, calcium oxide, magnesium oxide, scandium oxide, gadolinium oxide and strontium oxide.

As is conventional, the porous part of the surface of the second hollow electrode is conveniently located at the tip of the exposed end of this electrode. Preferably this porous tip of the second hollow electrode comprises a plug of porous ceramic such as porous zirconia. The non-porous part of the hollow second electrode may conveniently be formed of alumina, preferably of high-density alumina tube.

DETAILED DESCRIPTION OF THE DRAWING

Figure 1:
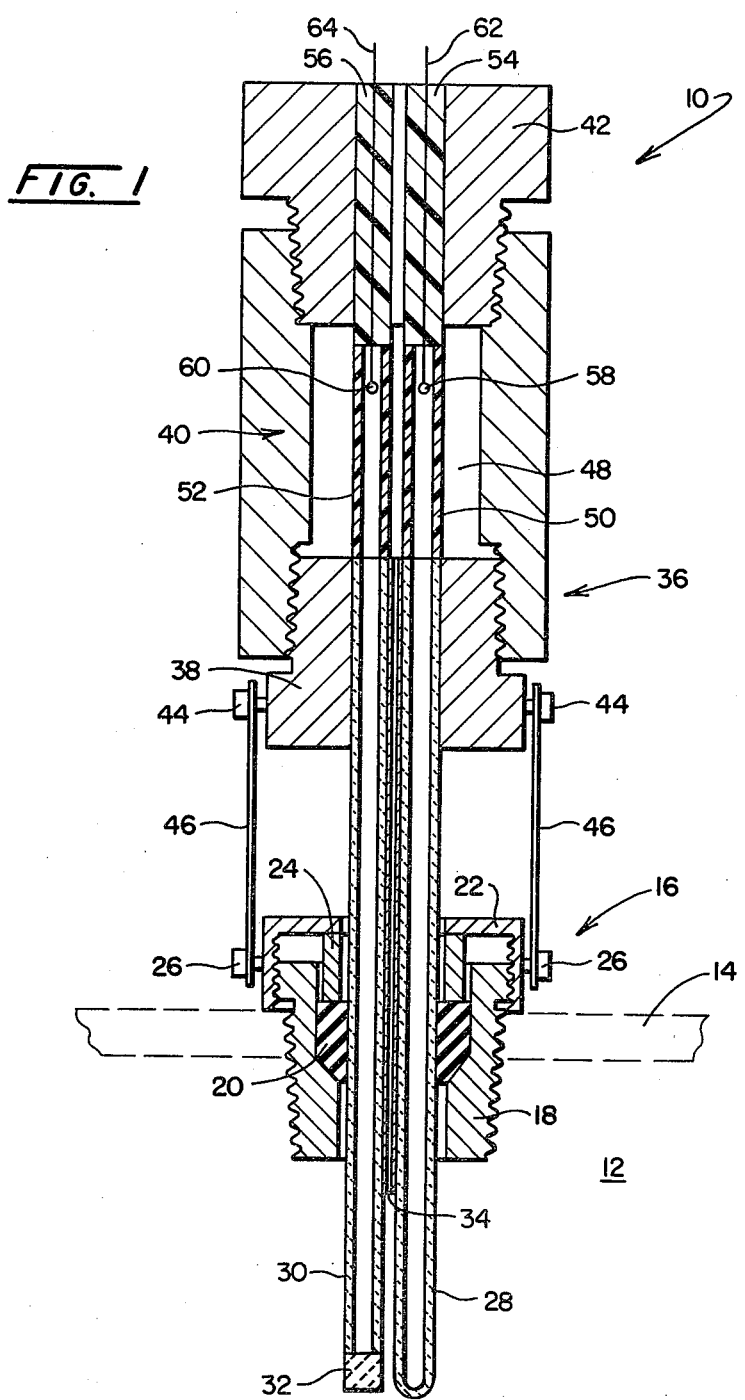
FIG. 1 is a cross section through a preferred apparatus of the invention.
Figure 3:
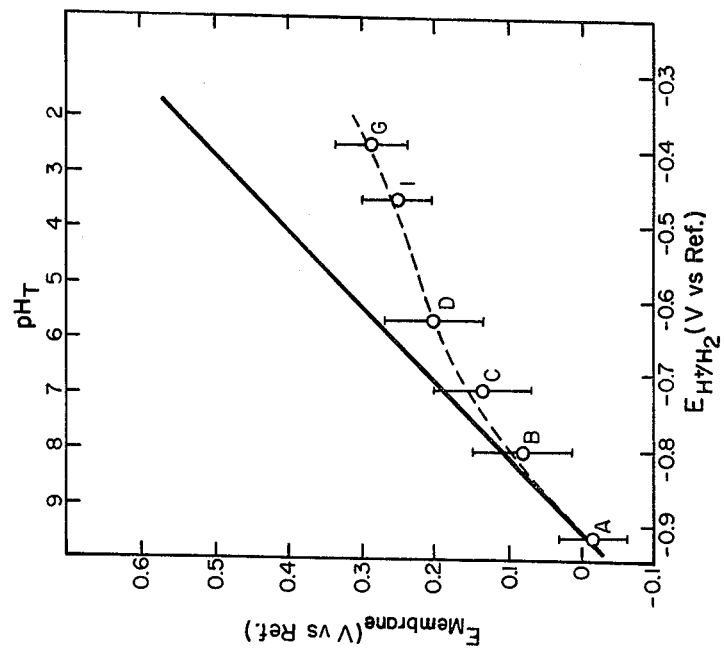
FIGS. 3–9 are graphs showing the potentials recorded by the electrode shown in FIG. 1 with various test solutions, as described in more detail below.

The preferred apparatus shown in FIG. 1 and generally designated 10 is used for determining the pH of a solution 12 which may be at a temperature of up to about 340° C. and which is contained under pressure within a container, part of the wall of which is shown in broken lines at 14. The solution at 12 may be, for example water being circulated in a steam-based power generation plant, "mud" used to lubricate oil well drilling rigs, a solution contained within a pipe in a chemical plant, or a brine used as a heat source in a geothermal power station.

The apparatus 10 comprises an electrode holder (generally designated 16). This electrode holder 16 comprises a conventional Conax (Registered Trade Mark) fitting 18 which protrudes through the wall 14 into the solution 12 and a Rulon (trademark) seal 20 which is retained within the fitting 18. A cap 22 screw threadedly engages the portion of the fitting 18 which extends outwardly beyond the wall 14 and has a downwardly extending cylindrical portion 24 which engages the upper end of the seal 20 thereby retaining the seal 20 in position. The outer cylindrical surface of the cap 22 bears two studs 26.

A hollow first electrode 28 formed of an oxide ion conducting zirconia/yttrium oxide ceramic is held in position by the electrode holder 16 so that the closed lower end of the electrode 28 extends clear of the lower end of the fitting 18 into the solution 12. A hollow second electode 30 is held by the electrode holder 16 in spaced, side-by-side relationship with the electrode 28. The main portion of the electrode 30 is formed of high-density alumina tube, but the tip of the electrode 30, which lies close to the closed lower end of electrode 28, is formed of a plug 32 of porous zirconia ceramic. Finally, the electrode holder 16 also retains in position a capillary tube 34 which extends between and parallel to the electrodes 28 and 30.

The apparatus shown in the accompanying drawing also comprises an enclosure member (generally designated 36), having three main sections, namely a lower Conax fitting 38, a central cylindrical section 40 and an upper Conax fitting 42. The lower fitting 38 is provided with bores which accommodate the upper ends of the electrodes 28 and 30 and the upper end of the capillary tube 34. It will be seen that the upper ends of the electrodes 28 and 30 are open and lie flush with the upper face of the fitting 38, whereas the upper end of the tube 34, which is also open, protrudes slightly above the upper face of the fitting 38. The fitting 38 is provided with studs 44 identical to the studs 26 on the cap 22. The studs 26 and 44 are joined by two insulated support straps 46, which act as thermal insulating means thermally insulating the enclosure member 36 from the high temperatures reached by the electrode holder 16 because of its contact with the hot solution 12.

The three sections of the enclosure member 36 together define a substantially cylindrical chamber 48. Within this chamber 48 are disposed first and second flexible-walled members 50 and 52 respectively having the form of hollow cylinders formed of flexible polytetrafluoroethylene (PTFE) film. The lower end of the first cylinder 50 fits sealingly around the upper end of the first electrode 28, while the upper end of the first cylinder 50 fits sealingly around the lower end of a first plug 54 which closes a bore formed in the upper fitting 42. Similarly, the lower end of the second cylinder 52 fits sealingly around the upper end of the second electrode 30, while the upper end of the second cylinder 52 fits sealingly around the lower end of a plug 56 disposed in a second bore in the upper fitting 42. Thus, the chambers formed in the interiors of these cylinders 50 and 52 communicate with the interiors of the hollow electrodes 28 and 30 respectively but are otherwise fluid-tight, so that no liquid can pass from the chamber 48 into or out of the chambers lying within the cylinders 50 and 52.

The two chambers formed by the hollow interiors of the electrodes 28 and 30 and the chambers within the cylinders 50 and 52 communicating therewith are filled with the same potassium chloride buffer solution consisting of 0.5 M potassium chloride, 0.01 M boric acid and 0.01 M potassium hydroxide. This potassium chloride buffer is in contact with first and second measuring electrodes 58 and 60 respectively located within the cylinders 50 and 52 respectively. The measuring electrodes 58 and 60 are both silver/silver chloride electrodes. It will be appreciated that a buffered potassium bromide or potassium iodide solution might be used within the electrodes 28 and 30, in which case the measuring electrodes 58 and 60 would be of silver/silver bromide or silver/silver iodide respectively. The measuring electrodes 58 and 60 are connected by leads 62 and 64 respectively passing through the plugs 54 and 56 respectively to an external circuit for potential measurement.

As already stated, the insulating straps 46 enable the enclosure member 36 to remain at substantially at room temperature despite the high temperatures reached by the electrode holder 16. The ceramic materials used to form the electrodes 28 and 30 are, of course, good thermal insulators so that no substantial heat conduction takes place along these electrodes. Although the capillary tube 34 is open at both ends, the thermal diffusion of heat therealong is small and since (as explained in more detail below) the pressure in the chamber 48 is maintained equal to the pressure of the solution 12, there is no tendency for the solution 12 to stream along the tube 34, and thus the entry of hot solution 12 into the chamber 48 is avoided. Accordingly, the fluid within the chamber 48 and that within the cylinders 50 and 52 in contact with the electrodes 58 and 60 stays substantially at room temperature and no thermal hydrolysis of the electrodes 58 and 60 occurs. This permits the apparatus to be operated for long periods with the electrodes 28 and 30 in contact with very hot solutions without any need to replace the electrodes 58 and 60.

The capillary tube 34 serves to ensure that the pressure within the chamber 48 remains substantially equal to the pressure of the solution 12. Although the PTFE cylinders 50 and 52 are fluid-impervious so that no fluid can enter or leave the cylinders 50 and 52 from the chamber 48, the flexible walls of the cylinders 50 and 52 ensure that the pressures within those cylinders are equal to that within the chamber 48, and thus equal to that of the solution 12. Also, since the chambers within the cylinders 50 and 52 are in fluid communication with the interiors of the electrodes 28 and 30 respectively, the pressures within the interiors of those electrodes are also equal to the pressure of the solution 12, and thus there is no tendency for fluid to stream through the porous zirconia plug 32. Accordingly, errors in measurement due to movement of fluid through the plug 32 are avoided, as is mixing of the buffered potassium chloride solution within the electrode 30 with the solution 12. Incidentally, it should be noted that the flexible walls of the cylinders 50 and 52 can deform outwardly to allow for the expansion of the solution within the interiors of the electrodes 28 and 30 which occurs when those electrodes are first placed in contact with the solution 12; the flexing of the walls of the cylinders 50 and 52 also, of course, allows for changes in the volume of the buffered potassium chloride solution consequent upon changes in the temperature of the solution 12.

The use of the same buffered potassium chloride solution in both electrodes 28 and 30 eliminates thermal diffusion potentials which might otherwise occur if a temperature difference exists between the tip of the ceramic membrane and the Ag/Ag Cl electrodes. That the use of the same buffered potassium chloride solution in both electrodes does eliminate the effect of thermal diffusion potential may be seen by considering the formal representation of the cell:

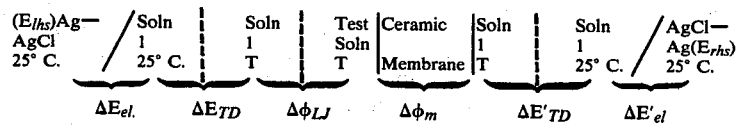

The measured potential $E_{rhs} - E_{lhs}$ is therefore $$\Delta E = \Delta E_{el} - \Delta E'_{el} + \Delta E_{TD} - \Delta E'_{TD} + \Delta \phi_{LJ} + \Delta \phi_m$$

where $\Delta E_{el}$ and $\Delta E'_{el}$ are the reversible potentials for the Ag/AgCl couples, $\Delta E_{TD}$ and $\Delta E'_{TD}$ are the thermal diffusion potentials associated with the non-isothermal solutions contained within the alumnia and $ZrO_2(Y_2O_3)$ ceramic tubes, respectively, $\Delta \phi_{LJ}$ is the isothermal liquid junction potential across the porous zirconia liquid junction, and $\Delta \phi_m$ is the pH-dependent membrane potential. Because the solutions contained in the two tubes are identical, $\Delta E_{el} = \Delta E'_{el}$ and $\Delta E_{TD} = \Delta E'_{TD}$ so that the measured potential is $\Delta E = \Delta \phi_{LJ} + \Delta \phi_m$. Furthermore, because the solution within the alumina tube contains a high concentration of KCL, $\Delta \phi_{LJ} \simeq 0$. Accordingly, the measured potential $\Delta E$ is substantially equal to the pH-dependent membrane potential. The construction of the preferred embodiment of the invention, in which the electrodes 28 and 30 are of substantially the same type and lie in spaced, side-by-side relationship, also ensures that to a high degree of accuracy the thermal gradients along the two electrodes are as nearly matched as possible so that the condition $\Delta E = \Delta \phi_m$ is substantially true regardless of the temperature of the solution 12.

Figure 2:
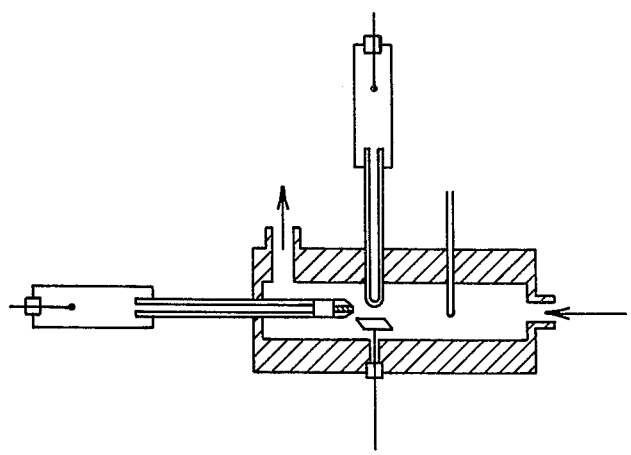
FIG. 2 is a schematic cross section through a test cell used to conduct experiments with the electrode shown in FIG. 1.
Figure 5:
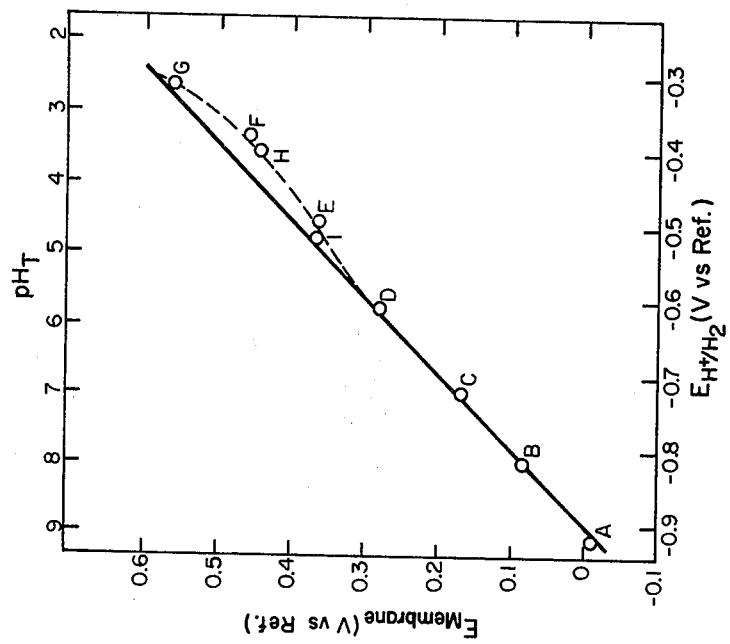
Figure 4:
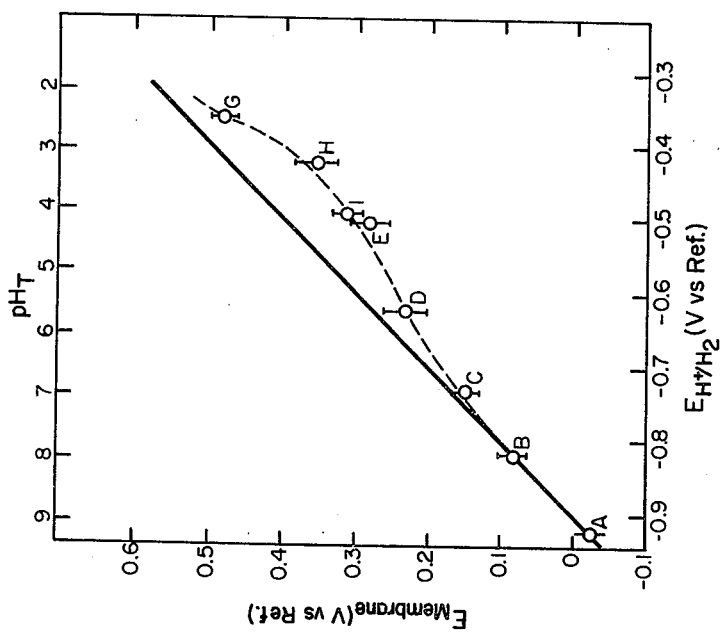
Figure 7:
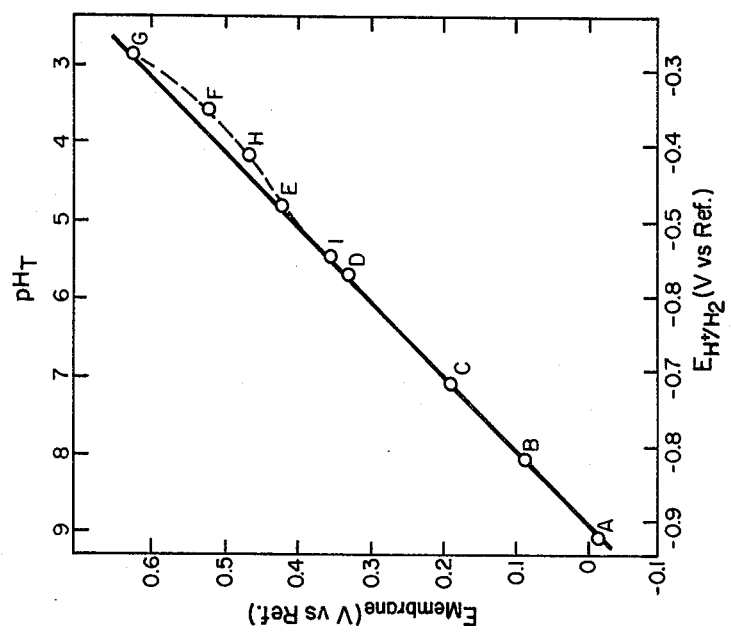
Figure 6:
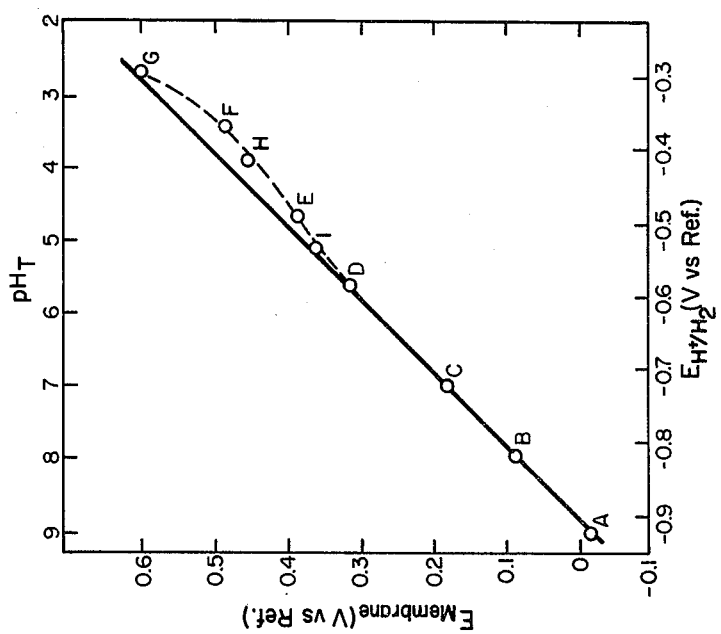

To calibrate the electrode shown in FIG. 1, the test cell shown in FIG. 2 was employed. It will be appreciated that the physical spatial relationship of the electrodes 28 and 30 is shown in FIG. 1 and the separation of these electrodes in FIG. 2 is made purely for purposes of illustration. The test cell (generally designated 70" was machined from stainless steel and was located immediately downstream of a one liter autoclave (not shown) which served as a heat source. The autoclave was provided with a recirculating loop arrangement which circulated test solution through the test cell as shown in FIG. 2. The test cell not only contained the electrodes 28 and 30 of the apparatus shown in FIG. 1, but also a platinized platinum hydrogen electrode of conventional type, so that the readings from the apparatus of the invention could be compared with those from this conventional electrode. The same potential difference was applied between the reference electrode 30 and the electrode 28 on the one hand and the platinum electrode on the other. Besides being compared with the readings from the electrode 28, the platinum electrode was used to measure the pH of solutions directly in those cases where the test cells contained hydrogen of known fugacity. In addition to the platinum electrode 72, the test cell was also provided with a thermocouple 74 to measure the temperature of the test solutions.

A reservoir was provided for storage of the solution before its circulation through the high temperature zone comprising the autoclave and test cell, and this reservoir was continually purged with hydrogen gas. The fugacity of the hydrogen in the single liquid phase passing through the test cell was calculated from the known Henry's Law constants in a known manner.

The potentials between the electrodes were measured using a Keithley 602 electrometer having an input impedance of $10^{14}$ ohms. Care was taken to ensure that the pH of poorly buffered solutions was stable before data was collected; during measurements of the pH of these poorly buffered solutions, small drifts in the pH with time were noted. These drifts can be attributed to the removal of carbon dioxide from the solution due to the continuous purging of the reservoir with hydrogen.

Nine different tests solutions were tested at temperatures of 100°, 150°, 200°, 225°, 250° and 275° C. These solutions ranged from buffered alkaline solutions containing potassium hydroxide and boric acid, through solutions containing sulfuric acid alone to solutions containing both sulfuric acid and sodium sulphate. The compositions of the test solutions are shown in the table below.

FIGS. 3–8 show the membrane potentials obtained at temperatures of 100°, 150°, 200°, 225°, 250° and 275° C. respectively as a function of the pH values of the various test solutions, these values being calculated from the hydrogen electrode potentials and the known fugacity of hydrogen in the system. The error bars associated with some of the membrane potential points in FIGS. 3–8 indicate the ranges over which the membrane potential was found to fluctuate due to high impedance of the membrane, particularly at lower temperatures.

The membrane electrode potentials plotted in FIGS. 3–8 demonstrate that the membrane does not exhibit a strictly nernstian pH response, particularly at lower temperatures; however, the deviation from nernstian behavior (as indicated by the solid lines in FIGS. 3–8) is most pronounced in weakly acidic solutions having pH's of 3–5 and decreases rapidly with increasing temperature. Despite this "acid error" of the electrode (which may be compared with the "alkaline error" of a conventional glass electrode) the behavior of the electrode was reproducible so that it could be used practically for measuring the pH of high-temperature aqueous solutions, being especially advantageous at temperatures above about 200° C.

The membrane electrode potential data shown in FIGS. 3–8 are reproduced in numerical form in the table below:

TABLE

| Solution | Composition | Temp. (°C.) | | | | | | |
|---|---|---|---|---|---|---|---|---|
| | | 25 | 100 | 150 | 200 | 225 | 250 | 275 |
| A | 0.01M KOH + 0.01M B(OH)$_3$ | —$^a$ $-913^b$ | $-15 \pm 50$ $-918$ | $-22 \pm 20$ $-926$ | $-8$ $-924$ | $-14$ $-924$ | $-12$ $-925$ | $-8$ $-922$ |
| B | $10^{-3}$M KOH + 0.01M B(OH)$_3$ | — $-776$ | $-80 \pm 70$ $-804$ | $-85 \pm 20$ $-822$ | $+85$ $-821$ | $+88$ $-817$ | $+86$ $-822$ | $+88$ $-821$ |
| C | $10^{-4}$M KOH + 0.01M B(OH)$_3$ | — $-714$ | $-135 \pm 70$ $-724$ | $-150 \pm 20$ $-738$ | $+168$ $-728$ | $+182$ $-726$ | $+185$ $-722$ | $+192$ $-714$ |
| D | 0.01M B(OH)$_3$ | — $-620$ | $+200 \pm 70$ $-630$ | $+230 \pm 30$ $-630$ | $+279$ $-618$ | $+312$ $-592$ | $+324$ $-580$ | $+340$ $-565$ |
| E | 0.00005 H$_2$SO$_4$ | — — | — — | $-280 \pm 30$ $-512$ | $362$ $-505$ | $+382$ $-498$ | $+412$ $-486$ | $+448$ $-454$ |
| F | 0.00005M H$_2$SO$_4$ | — — | — — | $-350 \pm 30$ $-430$ | $+454$ $-395$ | $+480$ $-378$ | $+510$ $-362$ | $+534$ $-351$ |
| G | 0.005M H$_2$SO$_4$ | — $-434$ | $+285 \pm 50$ $-394$ | $-480 \pm 20$ $-366$ | $+558$ $-329$ | $+595$ $-305$ | $+610$ $-290$ | $+622$ $-283$ |
| H | 0.005M H$_2$SO$_4$ + 0.005 Na$_2$SO$_4$ | — — | — — | — — | $+441$ $-415$ | $+450$ $-425$ | $+455$ $-423$ | $+467$ $-432$ |
| I | 0.005M H$_2$SO$_4$ + | — | $+250 \pm 50$ | $+310 \pm 20$ | $+364$ | $+356$ | $+346$ | $+342$ |

TABLE-continued

| Solution | Composition | Temp. (°C.) | | | | | | |
|---|---|---|---|---|---|---|---|---|
| | | 25 | 100 | 150 | 200 | 225 | 250 | 275 |
| | 0.005 Na$_2$SO$_4$ | — | −466 | −498 | −526 | −542 | −553 | −563 |

Figure 9:
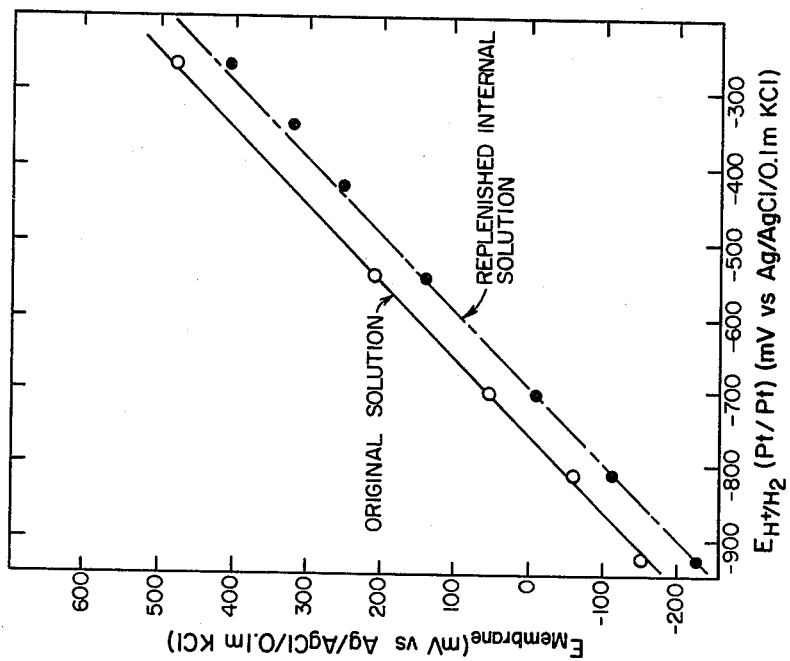
Figure 8:
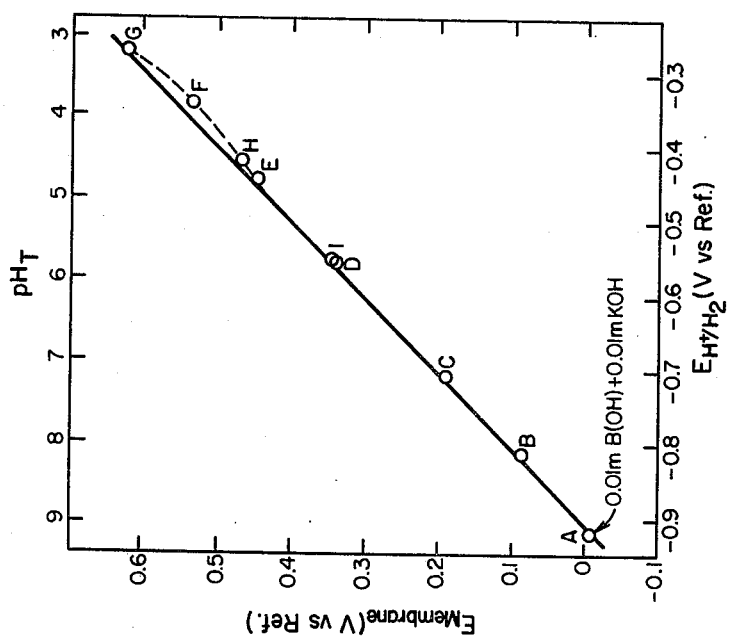

[a]Membrane potential vs pressure balanced external reference electrode
[b]Hydrogen electrode potential vs balanced external reference electrode A second series of experiments were carried out to illustrate the importance of employing a well-buffered solution within the instant apparatus. In this second series of experiments the 0.1 M potassium chloride/0.01 M boric acid/0.01 M potassium hydroxide internal solution used in the first series of experiments was replaced by a substantially unbuffered internal solution containing 0.1 M potassium chloride/0.01 M boric acid. After filling the apparatus with one batch of this solution, the apparatus was used to measure the pH's of solutions A–I in the table above at a temperature of 275° C. The first batch of solution was thereafter replaced with a second batch and the apparatus again used to measure the pH's of solutions of A–I at a temperature of 275° C. As shown in FIG. 9, both runs produced a linear correlation between membrane potential and pH, but the potentials recorded in the second run with replenished solution were displaced to more negative values by approximately 75 mV. This difference is attributable to reaction of the internal solution with the membrane itself, this reaction modifying the pH of the internal solution because of the poor buffering properties of boric acid alone. The effect was completely eliminated by adding 0.01 M potassium hydroxide to the internal solution as in the first series of experiments described above.

It will be appreciated that, like prior art ceramic membrane pH electrodes, the pH readings provided by the instant apparatus are not substantially affected by the redox potential of the solution 12 and thus the apparatus may be used to make accurate determinations of the pH of solutions whose redox potential may fluctuate.

It will be apparent to those skilled in the art that numerous variations and modifications may be made in the preferred embodiment of the invention described above. Accordingly, the foregoing description is to be construed in an illustrative and not in a limitative sense, the scope of the invention being defined solely by the appended claims.

I claim:

1. Apparatus for measuring the pH of a liquid at high temperatures and pressures, said apparatus comprising:
    a hollow first electrode formed at least in part of a ceramic capable of exhibiting a pH-dependent potential thereacross;
    a hollow second electrode, at least part of the surface of said second electrode being porous;
    a first flexible-walled member having walls defining a first chamber therewithin, said first chamber communicating with the interior of said hollow first electrode but being otherwise fluid-tight;
    a second flexible-walled member having walls defining a second chamber therewithin, said second chamber communicating with the interior of said hollow second electrode but being otherwise fluid-tight;
    first and second measuring electrodes disposed within said first and second chambers respectively;
    walls defining a third chamber enclosing said first and second flexible-walled members;
    pressure equalizing means for substantially equalizing the pressure of a medium surrounding the exterior surfaces of said first and second hollow electrodes and the pressure in said third chamber; and
    thermal insulating means for thermally insulating a medium surrounding said first and second flexible-walled members from the temperature of said medium surrounding said hollow first and second electrodes.

2. Apparatus according to claim 1 wherein said first chamber and the interior of said hollow first electrode, and said second chamber and the interior of said hollow second electrode, are both filled with the same buffered electrolyte solution.

3. Apparatus according to claim 2 wherein said buffered electrolyte solution comprises a buffered potassium chloride solution and said first and second measuring electrodes comprise silver/silver chloride electrodes.

4. Apparatus according to claim 1 wherein said hollow first and second electrodes are of elongate form and are disposed in spaced, side-by-side relationship, one end of each said hollow electrode being exposed for contact with said liquid and the opposed end of each said hollow electrode communicating with its associated flexible-walled member.

5. Apparatus according to claim 4 wherein said pressure equalizing means comprises a conduit extending from adjacent said exposed ends of said hollow electrodes to said third chamber.

6. Apparatus according to claim 4 wherein there is provided an electrode holder for retaining said hollow electrodes in said spaced side-by-side relationship and an enclosure member having said walls defining said third chamber, and wherein said thermal insulating means comprises at least one elongate, thermally-insulating strap connecting said electrode holder and said enclosure member.

7. Apparatus according to claim 4 wherein said porous part of the surface of said second hollow electrode is located at the tip of said exposed end of said second hollow electrode.

8. Apparatus according to claim 1 or 4 wherein said first hollow electrode is formed of a zirconia-based ceramic.

9. Apparatus according to claim 8 wherein said first hollow electrode is formed of a zirconia/yttrium oxide ceramic.

10. Apparatus according to claim 1 wherein said porous part of the surface of said second hollow electrode comprises a plug of porous ceramic.

11. Apparatus according to claim 10 wherein said porous ceramic comprises porous zirconia.

12. Apparatus according to claim 1 wherein the non-porous part of said second hollow electrode is formed of alumina.

* * * * *